(12) United States Patent
Nakanishi et al.

(10) Patent No.: US 9,358,321 B2
(45) Date of Patent: Jun. 7, 2016

(54) MEDICAL CERAMIC MATERIAL AND MANUFACTURING METHOD THEREOF

(71) Applicant: KYOCERA Medical Corporation, Osaka-shi, Osaka (JP)

(72) Inventors: Takefumi Nakanishi, Osaka (JP); Hironori Nagata, Osaka (JP)

(73) Assignee: KYOCERA Medical Corporation, Osaka (JP)

( * ) Notice: Subject to any disclaimer, the term of this patent is extended or adjusted under 35 U.S.C. 154(b) by 0 days.

(21) Appl. No.: 14/385,658

(22) PCT Filed: Feb. 28, 2013

(86) PCT No.: PCT/JP2013/055273
§ 371 (c)(1),
(2) Date: Sep. 16, 2014

(87) PCT Pub. No.: WO2013/136990
PCT Pub. Date: Sep. 19, 2013

(65) Prior Publication Data
US 2015/0038319 A1   Feb. 5, 2015

(30) Foreign Application Priority Data
Mar. 16, 2012 (JP) ................ 2012-061025

(51) Int. Cl.
*C04B 35/119* (2006.01)
*A61L 27/10* (2006.01)
*A61L 27/50* (2006.01)
(Continued)

(52) U.S. Cl.
CPC ........... *A61L 27/105* (2013.01); *A61L 27/045* (2013.01); *A61L 27/10* (2013.01); *A61L 27/425* (2013.01); *A61L 27/427* (2013.01); *A61L 27/50* (2013.01); *C04B 35/10* (2013.01); *C04B 35/119* (2013.01); *C04B 35/64* (2013.01); *A61L 2430/24* (2013.01); *C04B 2235/3275* (2013.01); *C04B 2235/602* (2013.01); *C04B 2235/9646* (2013.01); *C04B 2235/9661* (2013.01)

(58) Field of Classification Search
CPC ... C04B 35/119; A61L 27/427; A61L 27/105; A61L 27/045
See application file for complete search history.

(56) References Cited

U.S. PATENT DOCUMENTS

2008/0118722 A1   5/2008   Shikata et al.
2008/0275568 A1   11/2008  Shikata et al.

FOREIGN PATENT DOCUMENTS

JP   64-083565 A   3/1989
JP   02-302360 A   12/1990
(Continued)

OTHER PUBLICATIONS

Machine Transaltion of JP 2004059374, Feb. 2004.*
(Continued)

*Primary Examiner* — Karl Group
(74) *Attorney, Agent, or Firm* — Volpe and Koenig, P.C.

(57) ABSTRACT

The present invention provides a medical ceramic material with a color other than black or white, especially blue, with which it is possible to secure sufficient durability and to maintain a good appearance by sufficiently suppressing a color difference between before and after the irradiation of gamma-rays for sterilization. The medical ceramic material is formed using a composite material containing alumina and zirconia. The composite material contains cobalt oxide. The content of cobalt oxide is set to be 0.2 wt % to 1.0 wt % with respect to 100 wt % of the composite material excluding cobalt oxide.

5 Claims, 4 Drawing Sheets

(51) Int. Cl.
*A61L 27/42* (2006.01)
*C04B 35/10* (2006.01)
*C04B 35/64* (2006.01)
*A61L 27/04* (2006.01)

(56) References Cited

FOREIGN PATENT DOCUMENTS

| JP | 2000-191372 | A | | 7/2000 |
| JP | 2001-287987 | A | | 10/2001 |
| JP | 2004-059374 | A | | 2/2004 |
| JP | 2006-095018 | A | | 4/2006 |
| JP | 2006-122634 | A | | 5/2006 |
| JP | 2011020877 | | * | 2/2011 |
| WO | 2006/080473 | A1 | | 8/2006 |

OTHER PUBLICATIONS

Machine translatin of JP 2011010877, Feb. 2011.*
International Search Report, PCT/JP2013/055273, May 28, 2013, 2 pgs.

* cited by examiner

MEDICAL CERAMIC MATERIAL AND MANUFACTURING METHOD THEREOF

TECHNICAL FIELD

The present invention relates to a medical ceramic material used for an artificial joint or the like and a method for manufacturing the medical ceramic material.

BACKGROUND ART

There are cases where a medical component to be implanted in a living body is formed of a ceramic material. A zirconia sintered body for use as a medical material is known as such a ceramic material (see Patent Document 1, for example). The zirconia sintered body for use as a medical material described in Patent Document 1 contains tetragonal zirconia stabilized by $Y_2O_3$ as a main component. Moreover, this zirconia sintered body for use as a medical material has a configuration containing 0.05 to 0.5 parts by weight of both $SiO_2$ and $TiO_2$. With this configuration, the zirconia sintered body for use as a medical material is white, and is suppressed from changing its color from white when being sterilized by the irradiation of gamma-rays.

Also, a blackened zirconia ceramic for implantation in a living body is known as a medical ceramic material (see Patent Document 2, for example). Patent Document 2 discloses a configuration in which a deoxidation ratio of a material for this blackened zirconia ceramic is greater than 10 ppm. With this configuration, blackening of the blackened zirconia ceramic is realized. Moreover, since the deoxidation ratio is greater than 10 ppm, the color tone of the blackened zirconia ceramic is not substantially changed between before and after sterilization by the irradiation of gamma-rays.

CITATION LIST

Patent Documents

Patent Document 1: JP 2000-191372A ([0005] to [0007])
Patent Document 2: JP 2001-287987A ([0011] to [0013])

SUMMARY OF THE INVENTION

Technical Problem

After being implanted in a living body, the medical ceramic material is not visible directly from the outside of the living body. However, the medical ceramic material is arranged as a single item or in combination with other members before the medical ceramic material is implanted in a living body. Accordingly, it is preferable that the medical ceramic material has a good appearance (good aesthetic properties). Therefore, it is conceivable that the color of the medical ceramic material is a beautiful color free of dullness (blue, for example). On the other hand, the medical ceramic material is implanted in a living body, and therefore, it needs to be sterilized. That is, the ceramic material needs to be sterilized, for example, by the irradiation of gamma-rays as described above. However, generally, when the ceramic material is irradiated with gamma-rays, dullness (deterioration of the quality of the color tone) is generated in the ceramic material.

Patent Documents 1 and 2 disclose a configuration for suppressing the color tone from being changed due to sterilization by the irradiation of gamma-rays. However, Patent Documents 1 and 2 disclose no configuration for suppressing the color tone of the ceramic material with a color other than black or white from being changed due to the irradiation of gamma-rays.

Moreover, the medical ceramic material is often used in a living body for a long period of time, and therefore, sufficient durability is required.

The present invention was made in view of these circumstances, and it is an object thereof to provide a medical ceramic material with a color other than black or white, especially blue, with which it is possible to secure sufficient durability and to maintain a good appearance by sufficiently suppressing a color difference between before and after the irradiation of gamma-rays for sterilization.

Solution to Problem

In order to achieve the above-described object, a first aspect of the present invention is directed to a medical ceramic material formed using a composite material containing alumina and zirconia, in which the composite material contains cobalt oxide, and the content of the cobalt oxide is 0.2 wt % to 1.0 wt % with respect to 100 wt % of the composite material excluding the cobalt oxide.

In this aspect, the content of cobalt oxide is set to be 0.2 wt % to 1.0 wt %. Thereby, it is possible to secure sufficient durability of the medical ceramic material and to maintain its good appearance by suppressing a color difference between before and after the irradiation of gamma-rays for sterilization. When the content of cobalt oxide is less than 0.2 wt %, it is impossible to sufficiently increase the degree of coloring of the medical ceramic material by using cobalt oxide. Therefore, the color difference of the medical ceramic material due to the irradiation of gamma-rays is large, and therefore, there is a possibility that dullness generated in the medical ceramic material becomes clearly visible. Moreover, when the content of cobalt oxide is greater than 1.0 wt %, the crystal phase of a compound of alumina and cobalt is generated in the medical ceramic material. As a result, a mechanical strength, such as a fracture toughness, of the medical ceramic material is reduced, and the durability thereof is reduced.

Accordingly, with the present invention, it is possible to secure sufficient durability of the medical ceramic material, and to maintain its good appearance by sufficiently suppressing a color difference between before and after the irradiation of gamma-rays for sterilization.

A second aspect of the present invention is directed to the medical ceramic material according to the first aspect, in which the content of cobalt oxide is 0.2 wt % to 0.5 wt %.

In this aspect, the content of cobalt oxide is set to be 0.5 wt % or less. Thereby, it is possible to more reliably suppress the crystal phase of the compound of alumina and cobalt from being generated in the medical ceramic material. As a result, it is possible to further enhance the impact resistance, that is, the durability, of the medical ceramic material by suppressing the fracture toughness of the medical ceramic material from being reduced.

A third aspect of the present invention is directed to a method for manufacturing a medical ceramic material including a mixing step of mixing powders of at least alumina, zirconia and cobalt oxide to form a mixed powder, a pressing step of pressing the mixed powder to form a powder compact, and a firing step of firing the powder compact, in which the cobalt oxide is contained in the mixed powder in an amount of 0.2 wt % to 1.0 wt % with respect to 100 wt % of the mixed powder formed in the mixing step excluding the cobalt oxide.

In this aspect, the content of cobalt oxide in the mixed powder formed in the mixing step is set to be 0.2 wt % to 1.0 wt %. Thereby, it is possible to secure sufficient durability of the medical ceramic material and to maintain its good appearance by suppressing a color difference between before and after the irradiation of gamma-rays for sterilization. When the content of cobalt oxide is less than 0.2 wt %, it is impossible to sufficiently increase the degree of coloring of the medical ceramic material by using cobalt oxide. Therefore, the color difference of the medical ceramic material due to the irradiation of gamma-rays is large, and therefore, there is a possibility that dullness generated in the medical ceramic material becomes clearly visible. Moreover, when the content of cobalt oxide is greater than 1.0 wt %, the crystal phase of the compound of alumina and cobalt is generated in the medical ceramic material. As a result, a mechanical strength, such as a fracture toughness, of the medical ceramic material is reduced, and the durability thereof is reduced.

Accordingly, with the present invention, it is possible to provide a method for manufacturing the medical ceramic material in which sufficient durability can be secured and a good appearance can be maintained by sufficiently suppressing a color difference between before and after the irradiation of gamma-rays for sterilization.

A fourth aspect of the present invention is directed to the method for manufacturing the medical ceramic material according to the third aspect, in which the cobalt oxide in the mixing step includes tricobalt tetroxide.

With this aspect, it is possible to realize the medical ceramic material that is bright blue in color and has an excellent appearance.

Advantageous Effects of the Invention

With the present invention, it is possible to provide a medical ceramic material with a color other than black or white, especially blue, with which it is possible to secure sufficient durability and to maintain a good appearance by sufficiently suppressing a color difference between before and after the irradiation of gamma-rays for sterilization.

DESCRIPTION OF EMBODIMENT

Figure 1:
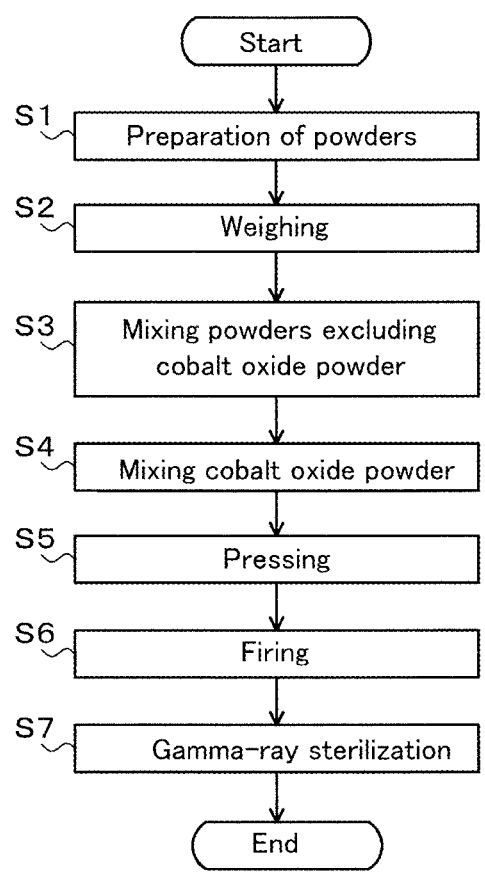
FIG. 1 is a flow chart for illustrating a method for manufacturing a medical ceramic material.

Hereinafter, an embodiment for carrying out the present invention will be described with reference to the drawings. It should be noted that the present invention is widely applicable as a medical ceramic material.

The medical ceramic material according to the embodiment of the present invention is used to form a medical component. A femoral head ball, an acetabular liner or the like of an artificial hip joint can be used as the medical component, for example. The liner is used as a member that is in contact with an artificial or an organic femoral head so as to be capable of sliding. The liner is formed in a shape that has an indentation for receiving the femoral head. The indentation is formed in a hemispherical shape, for example. The liner is generally held by the acetabular cartridge or the like via a shell made of metal. A load from the femoral head is applied to the liner. A relatively large load, such as the load of the upper half of the living body, is applied to the liner. The relatively large load means a load of several hundred N or more, for example. It is preferable that the medical ceramic material of this embodiment is used as a material for the medical component to which a relatively large load is applied in a living body in this manner.

The medical ceramic material is provided as a composite material containing alumina ($Al_2O_3$), zirconia ($ZrO_2$) and cobalt oxide. That is, the medical ceramic material is provided as an alumina-zirconia composite material and contains alumina and zirconia as the base materials.

It is preferable that the medical ceramic material further contains at least one of strontium oxide (SrO), silicon dioxide ($SiO_2$), titanium dioxide ($TiO_2$) and magnesium oxide (MgO).

The medical ceramic material is provided as a sintered body. More specifically, the medical ceramic material is manufactured by pressing mixed powder formed by mixing powders of the above-described materials using a mold and then firing it.

The total amount of alumina, zirconia, strontium oxide, silicon dioxide, titanium dioxide and magnesium oxide that are contained in the medical ceramic material is 100 wt % or less. In the medical ceramic material, the mass of the materials excluding cobalt oxide is 100 wt %.

It is preferable that the content of alumina in the medical ceramic material is 65 wt % or more. By setting the content of alumina to this, it is possible to realize the medical ceramic material that has an excellent biocompatibility, a high hardness and a high strength.

It is preferable that the content of zirconia in the medical ceramic material is 4 wt % to 34 wt %. By setting the lower limit of the content of zirconia to the above-described value, it is possible to secure the sufficient strength, such as a fracture toughness, of the medical ceramic material. It should be noted that a fracture toughness means a criterion for indicating resistance against a brittle fracture of a material. Moreover, by setting the upper limit of the content of zirconia to the above-described value, it is possible to suppress the hardness from being reduced due to the reduction of Young's modulus.

It is preferable that the content of strontium oxide in the medical ceramic material is 0.1 wt % to 4.0 wt %. By setting the lower limit of the content of strontium oxide to the above-described value, it is possible to suppress the monoclinic component of zirconia from being increased. Thereby, it is possible to secure the sufficient strength of the medical ceramic material. Moreover, by setting the upper limit of the content of strontium oxide to the above-described value, it is possible to suppress the temperature at which the medical ceramic material is fired from being increased. As a result, it is possible to suppress the densification from being inhibited by the formation of shape-anisotropic particles and the strength or the hardness from being reduced due to the growth of zirconia particles.

Furthermore, by adding silicon dioxide, titanium dioxide and magnesium oxide at a certain ratio, when the alumina and the zirconia are fired, it is possible to densify the sintered body at a low temperature while the crystal particles are suppressed from growing. As a result, it is possible to obtain the sintered body that is formed to have a structure with a small particle diameter and a high density. Thereby, it is possible to further enhance the strength of the medical ceramic material.

It is preferable that the content of silicon dioxide in the medical ceramic material is 0.20 wt % or more. It is preferable that the content of titanium dioxide is 0.22 wt % or more. It is preferable that the content of magnesium oxide in the medical ceramic material is 0.12 wt % or more. Thereby, it is possible to secure a sufficient liquid phase when the medical ceramic material is fired, and, as a result, it is possible to sufficiently densify the alumina.

It is preferable to add silicon dioxide, titanium dioxide and magnesium oxide as sintering auxiliary agents at the above-described ratio. Thereby, the strontium oxide is promoted to form a solid solution with the zirconia. As a result, it is possible to further enhance the strength and toughness of the medical ceramic material. Moreover, since a eutectic point becomes 1300° C. or less and a liquid phase is generated during sintering, the sintering of the materials is largely promoted. Therefore, it is possible to obtain a sintered body with a high denseness even at a lower sintering temperature. Moreover, it is possible to suppress anisotropic particles from growing by sintering at a relatively low temperature. As a result, the medical ceramic material has a fine structure, and therefore, it is possible to secure the sufficient strength and hardness.

As described above, it is possible to realize the medical ceramic material with a high strength, high toughness and high hardness when the medical ceramic material contains alumina of 65 wt % or more, zirconia of 4 to 34 wt %, strontium oxide of 0.1 to 4 wt %, silicon dioxide of 0.20 wt % or more, titanium dioxide of 0.22 wt % or more and magnesium oxide of 0.12 wt % or more, and the total content of silicon dioxide, titanium dioxide and magnesium oxide is 0.6 wt % to 4.5 wt %. It should be noted that the total content of the above-described substances is set to be 100 wt % or less.

In the medical ceramic material, cobalt oxide is provided as a coloring material for the medical ceramic material. The medical ceramic material is constituted by the sintered body containing cobalt oxide and thus has a blue appearance. At least one of tricobalt tetroxide ($CO_3O_4$), cobalt (II) oxide (CoO) and cobalt (III) oxide ($CO_2O_3$) can be used as the cobalt oxide of the medical ceramic material, for example.

It is preferable that the content of cobalt oxide in the medical ceramic material is set to be 0.2 wt % to 1.0 wt % with respect to 100 wt % of the components excluding the cobalt oxide. By setting the lower limit of the content of cobalt oxide to the above-described value, it is possible to sufficiently increase the degree of blueness in the medical ceramic material. As a result, even when the medical ceramic material is irradiated with gamma-rays in order to be sterilized, it is possible to sufficiently reduce the color difference value of the medical ceramic material between before and after the irradiation of gamma-rays. That is, even when the medical ceramic material is irradiated with gamma-rays, it is possible to more reliably suppress the visually noticeable dullness from being generated. Moreover, by setting the upper limit of the content of cobalt oxide to the above-described value, it is possible to maintain the mechanical strength of the medical ceramic material at a sufficiently high value. For example, when the content of cobalt oxide is greater than 1.0 wt %, the crystal phase of a compound of alumina and cobalt ($CoAl_2O_4$) is generated in the medical ceramic material. Thereby, the fracture toughness value of the medical ceramic material becomes low.

It should be noted that the upper limit of the content of cobalt oxide in the medical ceramic material is preferably 0.5 wt %. By setting the upper limit of the content of cobalt oxide to this, it is possible to more reliably suppress the crystal phase of the compound of alumina and cobalt from being generated. As a result, it is possible to more reliably suppress the fracture toughness value of the medical ceramic material from being reduced due to the crystal phase.

It is preferable that in the medical ceramic material, the average particle diameters of the powders of the above-described materials are 1.0 μm or less. Moreover, it is preferable that the firing temperature is 1300° C. to 1500° C. when the mixed powder obtained by mixing the powders of the above-described materials of the medical ceramic material is fired.

Next, a method for manufacturing the medical ceramic material will be described. FIG. 1 is a flow chart for illustrating the method for manufacturing the medical ceramic material. As shown in FIG. 1, when the medical ceramic material is manufactured, first, powders used as the materials for forming the medical ceramic material are prepared (step S1). Specifically, powders of alumina, zirconia, cobalt oxide (tricobalt tetroxide $Co_3O_4$), strontium oxide, silicon dioxide, titanium dioxide and magnesium oxide are prepared.

Next, the powders of the materials are weighed (step S2). Specifically, alumina, zirconia, cobalt oxide, strontium oxide, silicon dioxide, titanium dioxide and magnesium oxide are weighed so that the contents thereof in the medical ceramic material meet the above-described conditions in terms of wt %.

Next, the powders excluding cobalt oxide powder of the weighed powders of the materials are mixed (step S3). Thereby, the powders other than cobalt oxide powder of the weighed powders of the materials are uniformly mixed. Thereafter, the weighed powder of the cobalt oxide is further mixed in the uniformly mixed powders (step S4). Thereby, a mixed powder as a material for forming the medical ceramic material is completed.

Next, the mixed powder is pressed (step S5). Specifically, a cavity of a predetermined mold such as a metal mold is filled up with the mixed powder. The mold is used to form the above-described medical component. The mixed powder is pressed in the mold, for example, at a pressure of 100 MPa. It should be noted that in the pressing step, a cold isostatic pressing (CIP) is preferably performed, for example. Thereby, the mixed powder constitutes a powder compact with a shape of the medical component. That is, a powder compact is formed in the form of a solid body obtained by pressing the mixed powder to be compacted. If the cold isostatic pressing is performed, it is possible to make the density of the powder compact more uniform.

Next, the powder compact is fired (step S6). In this case, the firing temperature is set to a range of approximately 1300° C. to 1500° C. In some cases, a hot isostatic pressing (HIP) is performed. Thereby, the powder compact is formed into a sintered body. That is, the medical ceramic material is completed. It is possible to perform machining, such as cutting, grinding and polishing, which is omitted in FIG. 1, on the powder compact as needed before or after firing to provide a medical member with a desired shape. Next, the medical ceramic material is sterilized by gamma-rays (step S7). Generally, the amount of gamma-rays with which the medical ceramic material is irradiated is set to be approximately 25 kGy.

In the medical ceramic material described above, the content of cobalt oxide is set to be 0.2 wt % to 1.0 wt %. Thereby, it is possible to secure sufficient durability of the medical ceramic material and to maintain its beautiful blue appearance by suppressing a color difference between before and after the irradiation of gamma-rays for sterilization. When the content of cobalt oxide is less than 0.2 wt %, it is impossible to sufficiently increase the degree of coloring of the medical ceramic material by using cobalt oxide. Therefore, the color difference of the medical ceramic material due to the irradiation of gamma-rays is large, and therefore, there is a possibility that the dullness generated in the medical ceramic material becomes clearly visible. Moreover, when the content of cobalt oxide is greater than 1.0 wt %, the crystal phase of the compound of alumina and cobalt is generated in the medical ceramic material. As a result, the mechanical strength, such as a fracture toughness, of the medical ceramic material is reduced, and the durability thereof is reduced.

Accordingly, with the medical ceramic material of this embodiment, it is possible to secure sufficient durability and to maintain a beautiful blue appearance by sufficiently suppressing a color difference between before and after the irradiation of gamma-rays for sterilization.

Moreover, it is more preferable that the content of cobalt oxide in the medical ceramic material is 0.2 wt % to 0.5 wt %. By setting the content of cobalt oxide to 0.5 wt % or less in this manner, it is possible to more reliably suppress the crystal phase of the compound of alumina and cobalt from being generated in the medical ceramic material. As a result, it is possible to further enhance the impact resistance, that is, the durability, of the medical ceramic material by suppressing the fracture toughness of the medical ceramic material from being reduced.

Moreover, in the method for manufacturing the medical ceramic material, the cobalt oxide in the mixing step (step S4) includes tricobalt tetroxide. Thereby, it is possible to realize the medical ceramic material that is bright blue in color and has an excellent appearance.

Furthermore, the medical ceramic material of this embodiment has a blue appearance. Since most of conventional medical ceramic materials made of oxide ceramic containing alumina, zirconia or the like are white to light yellow in color, the medical ceramic material with the blue appearance is clearly distinguished from a conventional one so has the effect of preventing mistakes of use. Moreover, blue is known as a color which enhances the power of concentration. Accordingly, during an operation for installing an artificial joint component formed of the medical ceramic material in a patient, it is possible to enhance the power of concentration of a surgeon. Thereby, with the medical ceramic material, it is possible to provide a good environment in which a surgeon performs an operation.

In the description above, an embodiment of the present invention was described, but the present invention is not limited thereto, and various modifications may be made within the scope recited in the claims.

EXAMPLES

By performing steps S1 to S6 shown in FIG. 1 and then performing the irradiation of gamma-rays in step S7, Example 1 was manufactured. It should be noted that in step S7, the amount of gamma-rays with which the medical ceramic material was irradiated was 25 kGy. In addition, Examples 2, 3, 4 and 5 and Comparative Examples 1, 2 and 3 were manufactured in the same manner as Example 1. It should be noted that Examples 1 to 5 and Comparative Examples 1 to 3 have a disc shape (tablet shape). Moreover, when Examples 1 to 5 and Comparative Examples 1 to 3 were pressed, metallic molding was performed. Furthermore, Examples 1 to 5 and Comparative Examples 1 to 3 had the same components, except that the contents of cobalt oxide were varied. The contents of cobalt oxide in Examples 1 to 5 and Comparative Examples 1 to 3 with respect to 100 wt % of the components excluding the cobalt oxide were as follows.

Comparative Example 1: 0.0 wt %
Comparative Example 2: 0.1 wt %
Example 1: 0.2 wt %
Example 2: 0.3 wt %
Example 3: 0.4 wt %
Example 4: 0.5 wt %
Example 5: 1.0 wt %
Comparative Example 3: 3.0 wt %

Measurement of Color Difference Value

The color difference values of Examples 1 to 4 and Comparative Examples 1 to 3 before and after the irradiation of gamma-rays were measured. The color differences were measured using a spectrophotometer (CM-370d, manufactured by Konica Minolta, Inc.). Specifically, diffuse reflection factors of the surfaces of Examples 1 to 4 and Comparative Examples 1 to 3 were measured, and thereby, values in CIE (Commission Internationale de l'Eclairage) L*a*b* color system were obtained. Color differences were calculated from the obtained values.

It should be noted that a method for displaying colors was based on "Color specification—L*a*b* color system and L*u*v* color system" defined in JIS (Japanese Industrial Standard) Z8729 and "Color specification—Color differences of object colors" defined in JIS Z8730. L* means lightness, and a* and b* mean chromaticness indices. L*a*b* color system represents colors using coordinates of the L*a*b* on the color space. A color difference value ΔE is given by the following equation (1).

$$\Delta E = \{(dL^*)^2 + (da^*)^2 + (db^*)^2\}^{1/2} \quad (1)$$

It should be noted that ΔE is a color difference between before and after the irradiation of gamma-rays in Examples 1 to 4 and Comparative Examples 1 to 3 and indicates a distance in the color space. dL* is a lightness difference between before and after the irradiation of gamma-rays in Examples 1 to 4 and Comparative Examples 1 to 3. da* and db* is a chromaticness-index difference between before and after the irradiation of gamma-rays in Examples 1 to 4 and Comparative Examples 1 to 3.

It should be noted that in the measurement of color differences, three test specimens, under the same condition, of each of Examples 1 to 3 and Comparative Example 1 were manufactured, and the average value of the three measurement results was calculated. One specimen was measured in each of Example 4 and Comparative Examples 2 and 3.

Figure 2:
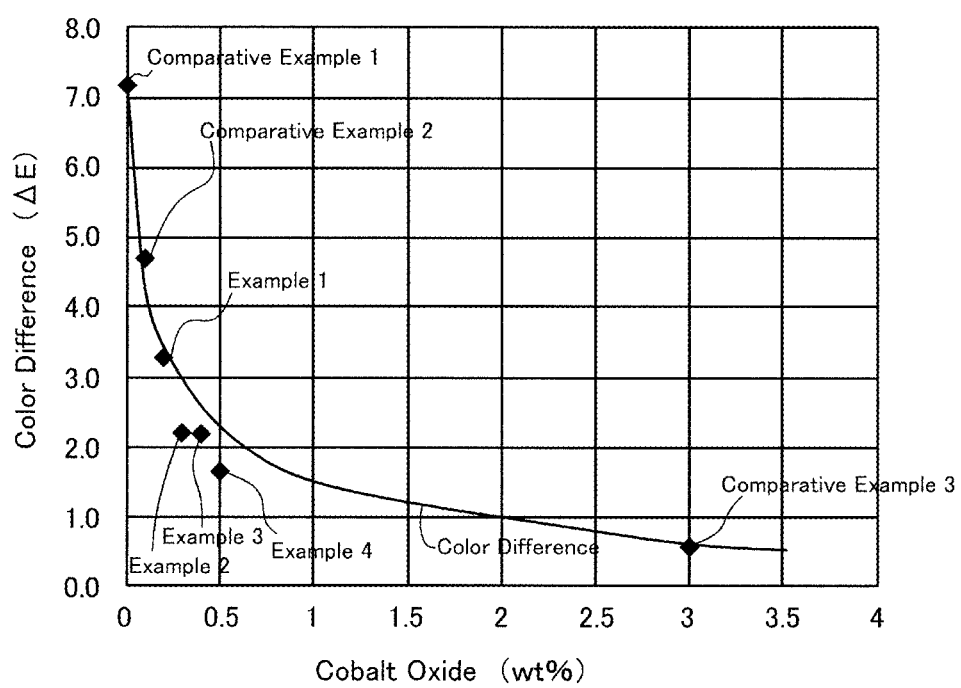
FIG. 2 is a graph illustrating a relationship between the content of cobalt oxide and a color difference $\Delta E$ between before and after the irradiation of gamma-rays.

Table 1 and FIG. 2 show the measurement results.

TABLE 1

|  | Cobalt oxide (wt %) | Color difference ΔE | Evaluation |
| --- | --- | --- | --- |
| Com. Ex. 1 | 0.0 | 7.2 | Poor |
| Com. Ex. 2 | 0.1 | 4.7 | Poor |
| Ex. 1 | 0.2 | 3.3 | Fair |
| Ex. 2 | 0.3 | 2.2 | Good |
| Ex. 3 | 0.4 | 2.2 | Good |
| Ex. 4 | 0.5 | 1.7 | Good |
| Com. Ex. 3 | 3.0 | 0.6 | Good |

FIG. 2 is a graph illustrating a relationship between the content of cobalt oxide and a color difference ΔE between before and after the irradiation of gamma-rays. It should be noted that the relationship between the content of cobalt oxide and a color difference ΔE shown in FIG. 2 is the same as the relationship between the content of cobalt oxide and a color difference ΔE shown in Table 1.

In FIG. 2, actually measured values showing the relationship between the content of cobalt oxide and a color difference ΔE are indicated by diamonds. In addition, in FIG. 2, a graph that is estimated based on the measurement results and shows the relationship between the content of cobalt oxide and a color difference ΔE is indicated by a solid line. Moreover, the evaluations of color differences ΔE are shown in Table 1. Specifically, when a color difference ΔE is greater than 3.5, the result is evaluated as "Poor" because the dullness of color (changes in color) due to the irradiation of gamma-rays is clearly visible. When a color difference ΔE is 3.0 or more to 3.5 or less, the result is evaluated as "Fair" because the dullness of color is substantially imperceptible. When a color difference ΔE is less than 3.0, the result is evaluated as "Good" because there is very little dullness of color and the dullness of color is much more imperceptible.

As shown in Table 1 and FIG. 2, when Comparative Example 1, which is the same as a conventional one, was measured, the color difference ΔE was 7.2, which was a large number, and was evaluated as "Poor". Since no cobalt oxide was added to Comparative Example 1, Comparative Example 1 was white before the irradiation of gamma-rays. However, the degree of the dullness of color due to the irradiation of gamma-rays was large, the dullness could be noticed at a glance, and the deterioration of the appearance due to the irradiation of gamma-rays was clearly confirmed.

Moreover, in Comparative Example 2, the color difference ΔE was 4.7, which was smaller than the color difference ΔE of 7.2 in the conventional one (Comparative Example 1), but the effect was not enough, and the evaluation was "Poor". In this manner, in Comparative Example 2, the degree of the dullness of color due to the irradiation of gamma-rays was still large, the dullness could be noticed at a glance, and the deterioration of the appearance due to the irradiation of gamma-rays was clearly confirmed.

On the other hand, the color difference ΔE of Example 1 was 3.3 and was evaluated as "Fair". The color difference ΔE of Example 1 was less than a half of the color difference ΔE of Comparative Example 1, to which no cobalt oxide is added. In this manner, in Example 1, it was possible to reliably suppress the degree of the dullness of color due to the irradiation of gamma-rays. Therefore, in Example 1, the dullness was substantially imperceptible and it was demonstrated that the appearance was suppressed from being deteriorated due to the irradiation of gamma-rays.

The color differences ΔE of Examples 2 and 3 were both 2.2 and were evaluated as "Good" because the color differences ΔE were further improved compared to that of Example 1.

Moreover, the color difference ΔE of Example 4 was 1.7 and was also evaluated as "Good". In this manner, in Examples 2, 3 and 4, it was possible to more reliably suppress the degree of the dullness of color due to the irradiation of gamma-rays, the dullness was imperceptible and it was demonstrated that the appearance was more reliably suppressed from being deteriorated due to the irradiation of gamma-rays.

Furthermore, the color difference ΔE of Comparative Example 3 was 0.6 and was evaluated as "Good" in the same manner as Examples.

As shown in FIG. 2, it is clear that even when the content of cobalt oxide is 1.0 wt %, the degree of the dullness of color is small after the irradiation of gamma-rays and the appearance before the irradiation of gamma-rays is maintained. As is clear from the above description, it is demonstrated that when the content of cobalt oxide is 0.2 wt % or more, the degree of the dullness of color is small after the irradiation of gamma-rays and the appearance before the irradiation of gamma-rays is maintained.

Measurement of Mechanical Properties

Next, mechanical properties of Examples 4 and 5 and Comparative Examples 1, 2 and 3 were measured. Specifically, densities, strengths (four-point flexural strengths), fracture toughness values and hardnesses (Vickers hardnesses) of Examples 4 and 5 and Comparative Examples 1, 2 and 3 were measured. A measurement method and a measurement condition are as follows.

Density: Bulk density was measured based on ISO 18754.

Four-point flexural strength: Four-point flexural strength was measured based on ISO 14704: 2008 under the condition with a crosshead speed of 0.5 mm/min, an upper span of 20 mm and the lower span of 40 mm.

Fracture toughness: Fracture toughness was measured based on ISO 15732 by the SEPB method using a test piece with a shape of 3×4×40 mm under the condition with an indentation load for a press of 98 N (one point) and by the three-point flexural test under the condition with the lower span of 30 mm and the crosshead speed of 0.5 mm/min.

Hardness: Hardness was measured by the Vickers hardness test based on ISO 14705 under the condition with a load for a press of 9.8 N and an applying time of 15 seconds.

Table 2 shows the results.

TABLE 2

| | Com. Ex. 1 | Com. Ex. 2 | Ex. 4 | Ex. 5 | Com. Ex. 3 |
|---|---|---|---|---|---|
| Cobalt oxide (wt %) | 0.0% | 0.1% | 0.5% | 1.0% | 3.0% |
| Density (g/m$^3$) | 4.25 | 4.25 | 4.24 | 4.25 | 4.26 |
| Strength (MPa) | 1145 | 1180 | 1129 | 1343 | 1364 |
| Fracture toughness (MPa·m$^{0.5}$) | 4.3 | 4.7 | 4.4 | 4.5 | 4.2 |
| Hardness (HV) | 1770 | 1730 | 1708 | 1694 | 1691 |

As shown in Table 2, Examples 4 and 5 and Comparative Examples 1, 2 and 3 had substantially the same densities. Moreover, the strengths of Examples 4 and 5 and Comparative Examples 1, 2 and 3 were greater than 1100 MPa and it was demonstrated that they have sufficient strengths.

As shown in Table 2, it was demonstrated that Examples 4 and 5 and Comparative Examples 1 and 2 have high fracture toughnesses of 4.3 MPa·m$^{0.5}$ or more. On the other hand, when Comparative Example 3 was measured, the fracture toughness was 4.2 MPa·m$^{0.5}$, which was the lowest toughness value, and it was demonstrated that Comparative Example 3 has a low fracture toughness. Also, Comparative Example 3 had the lowest hardness value (HV) in Examples 4 and 5 and Comparative Examples 1, 2 and 3, and it was demonstrated that Comparative Example 3 has a low hardness. In this manner, it became clear that when the content of cobalt oxide is greater than 1.0 wt %, the fracture toughness and hardness are slightly reduced.

Figure 3:
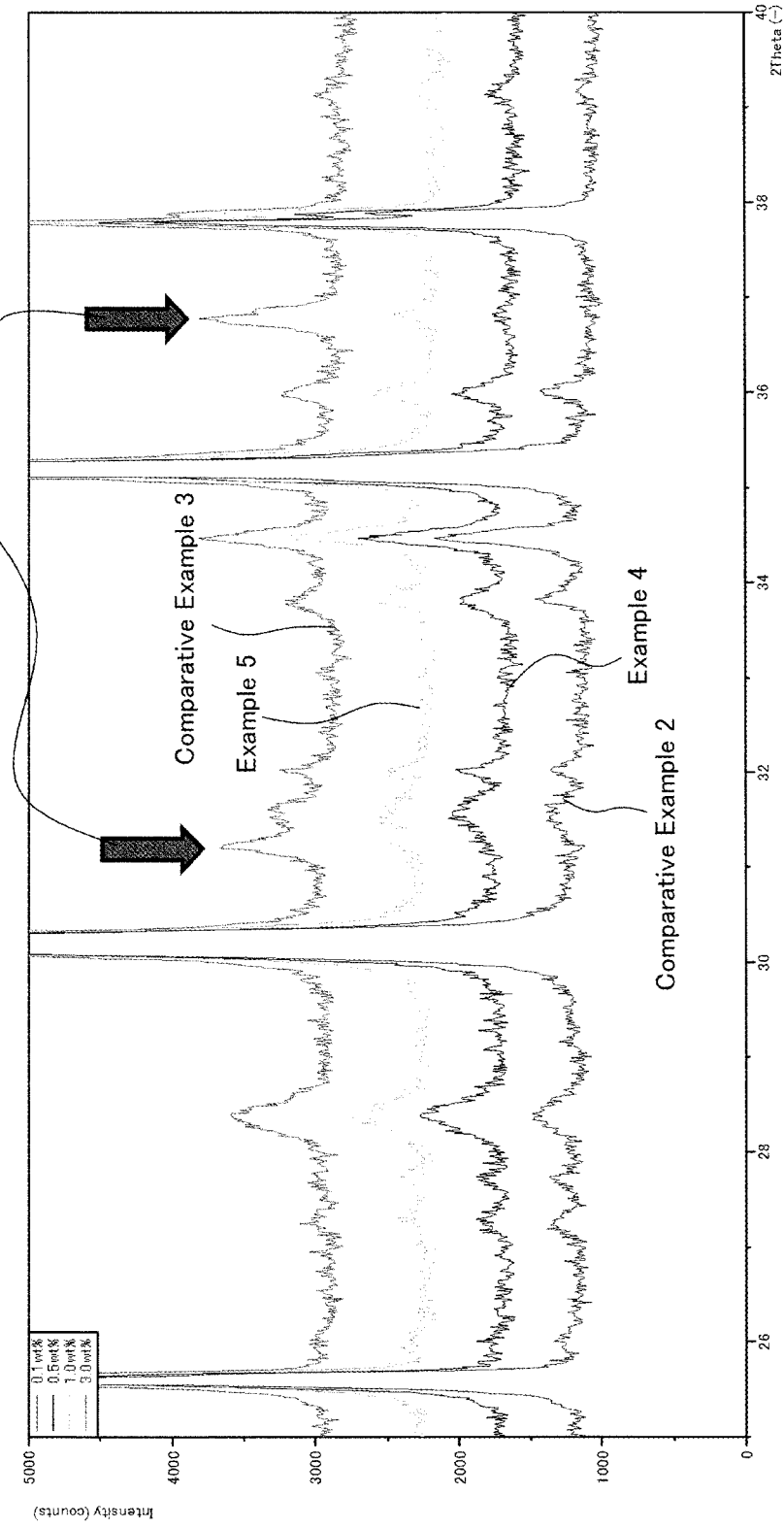
FIG. 3 shows graphs showing results of X-ray diffraction experiments of Examples 4 and 5 and Comparative Examples 2 and 3.

Next, X-ray diffraction experiments were performed on Examples 4 and 5 and Comparative Examples 2 and 3. FIG. 3 shows the results. FIG. 3 shows graphs showing the results of X-ray diffraction experiments of Examples 4 and 5 and Comparative Examples 2 and 3. In FIG. 3, the horizontal axis (2Theta) indicates a diffraction angle and the vertical axis (Intensity) indicates an X-ray intensity. When peaks appear at diffraction angles (2Theta) of approximately 31 degrees and approximately 37 degrees as shown in FIG. 3, it is possible to determine that the crystal phase of the compound of alumina and cobalt is generated.

In Comparative Example 2 that contains cobalt oxide of 0.1 wt % and Example 4 that contains cobalt oxide of 0.5 wt %, the content of cobalt oxide was small, and it was not recognized that peaks of the X-ray intensity appeared at both diffraction angles of approximately 31 degrees and approximately 37 degrees. Also, in Example 5 that contains cobalt oxide of 1.0 wt %, it was not recognized that peaks of the X-ray intensity appeared at a diffraction angle of approximately 31 degrees.

In Example 5, although the X-ray intensity slightly rose at a diffraction angle of approximately 37 degrees, it was not recognized that a well-defined peak appeared. It is conceivable that the crystal phase of the compound of alumina and cobalt ($CoAl_2O_4$) is present in a very small amount in Example 5.

On the other hand, in Comparative Example 3, it was recognized that well-defined peaks of the X-ray intensity appeared at both diffraction angles of approximately 31 degrees and approximately 37 degrees. That is, it became clear that the crystal phase of the compound of alumina and cobalt ($CoAl_2O_4$) is apparently present in Comparative Example 3. It is conceivable that the fracture toughness is reduced due to the presence of this crystal phase. That is, it is demonstrated from the measurement results of the mechanical properties shown in Table 2 and the results of the X-ray diffraction experiments shown in FIG. 3 that when the content of cobalt oxide is greater than 1.0 wt %, the fracture toughness is low and it is difficult to secure sufficient durability. In other words, it is demonstrated that when the content of cobalt oxide is 1.0 wt % or less, the fracture toughness is high and it is possible to secure sufficiently high durability.

Figure 4:
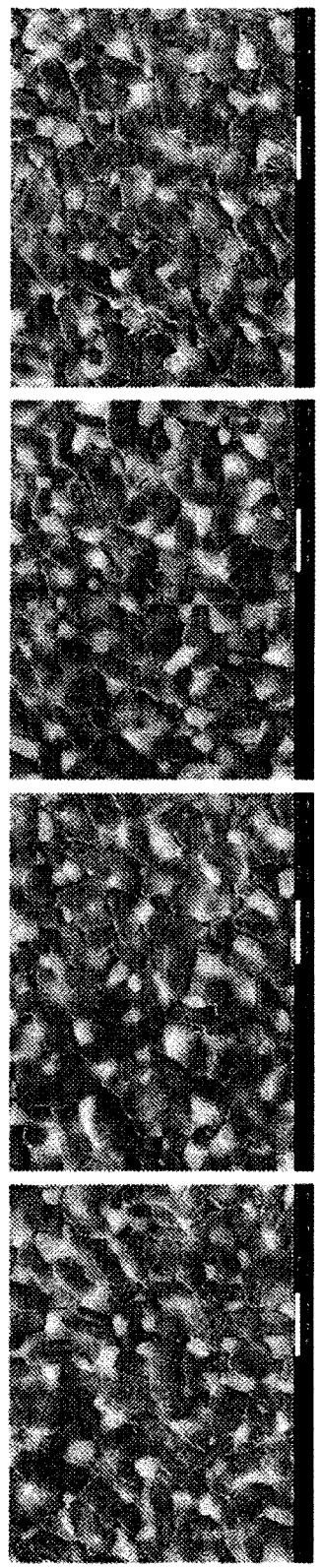
FIG. 4 shows images of the surfaces of Examples 4 and 5 and Comparative Examples 2 and 3 taken by an electron microscope.

FIG. 4 shows images of the surfaces of Examples 4 and 5 and Comparative Examples 2 and 3 taken by an electron microscope. As shown in FIG. 4, in Comparative Examples 2 and Examples 4 and 5, it is possible to clearly confirm borders between fine crystal particles constituting the composite polycrystalline ceramic of the present invention. This shows that the generation of some components (e.g., a crystal phase of a compound of alumina and cobalt ($CoAl_2O_4$)) excluding the main component between the particles (that is, at the particle boundaries) is not clearly recognized. On the other hand, the content of the cobalt oxide in Comparative Example 3 is 3.0 wt %, which is large, so that in the image of FIG. 4, the observation result is obtained in which the particle boundaries are blurred. It is conceivable that this is because the crystal phase of the compound of alumina and cobalt ($CoAl_2O_4$) is formed and exists at the particle boundaries. It is assumed that such changes in a fine structure cause the reduction of the fracture toughness and the hardness.

INDUSTRIAL APPLICABILITY

The present invention is widely applicable as a medical ceramic material used for an artificial joint or the like and a method for manufacturing the medical ceramic material.

The invention claimed is:

1. A medical ceramic material formed using a composite material containing alumina and zirconia, wherein
the composite material contains cobalt oxide, and the cobalt oxide is greater than 0.2 wt % to 1.0 wt % with respect to 100 wt % of the composite material excluding the cobalt oxide,
the composite material further contains titanium dioxide and at least one of strontium oxide, silicon dioxide, and magnesium oxide;
the composite materials are composed of particles with an average particle diameter of the particles of 1.0 micron or less; and
a color difference ($\Delta E$) measured in the medical ceramic is less than 3.5 after the medical ceramic undergoes gamma irradiation sterilization.

2. The medical ceramic material according to claim 1, wherein the cobalt oxide is greater than 0.2 wt % and less than 0.5 wt %.

3. A method for manufacturing a medical ceramic material comprising:
a mixing step of mixing powders of at least alumina, zirconia, cobalt oxide, and titanium dioxide and at least one of strontium oxide, silicon dioxide, and magnesium oxide to form a mixed powder;
a pressing step of pressing the mixed powder to form a powder compact; and
a firing step of firing the powder compact to form a sintered body,
wherein the cobalt oxide contained in the mixed powder is greater than 0.2 wt % and less than 1.0 wt % with respect to 100 wt % of the mixed powder formed in the mixing step excluding the cobalt oxide,
wherein a color difference ($\Delta E$) measured in the medical ceramic is less than 3.5 after the medical ceramic undergoes gamma irradiation sterilization
wherein an average particle diameter of the particles contained in the sintered body is 1.0 micron or less.

4. The method for manufacturing a medical ceramic material according to claim 3, wherein the cobalt oxide in the mixing step includes tricobalt tetroxide.

5. The medical ceramic material of claim 1, wherein the cobalt oxide includes tricobalt tetroxide.

* * * * *